United States Patent [19]

Boigegrain et al.

[11] Patent Number: 4,927,955

[45] Date of Patent: May 22, 1990

[54] PROCESS FOR THE O-ALKYLATION OF N-(HYDROXY)ARALKYLPHENYLE-THANOLAMINES

[75] Inventors: Robert Boigegrain, Castelnau Le Lez, France; Roberto Cecchi, Lodi-Milan; Sergio Boveri, Tortona, both of Italy

[73] Assignee: Sanofi, Paris, France

[21] Appl. No.: 230,860

[22] Filed: Aug. 11, 1988

[30] Foreign Application Priority Data

Aug. 12, 1987 [FR] France .............................. 87 11498
Jun. 14, 1988 [FR] France .............................. 88 07948

[51] Int. Cl.$^5$ ........................................ C07C 101/42
[52] U.S. Cl. ...................................... 560/45; 560/42; 560/27; 560/28
[58] Field of Search ...................... 560/42, 45, 27, 28

[56] References Cited

U.S. PATENT DOCUMENTS

| | | | |
|---|---|---|---|
| 3,781,328 | 12/1973 | Witte et al. | 560/42 |
| 4,275,219 | 6/1981 | Zupan | 560/29 |
| 4,338,333 | 7/1982 | Ainsworth et al. | 514/539 |
| 4,382,958 | 5/1983 | Duckworth | 514/653 |
| 4,707,497 | 11/1987 | Cecchi et al. | 514/647 |

FOREIGN PATENT DOCUMENTS 0023385  2/1981  European Pat. Off. .
0052963  6/1982  European Pat. Off. .
211721  2/1987  European Pat. Off. .
WO81/00849  4/1981  PCT Int'l Appl. .

Primary Examiner—Bruce Gray
Attorney, Agent, or Firm—Bacon & Thomas

[57] ABSTRACT

A process for the preparation of a compound of formula

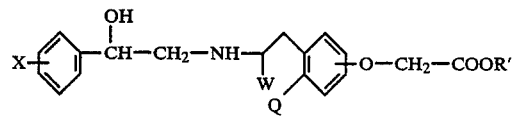

wherein X represents hydrogen, halogen, trifluoromethyl or lower alkyl group; W represents methyl, Q represents hydrogen or W and Q, together, form an ethylene group and R' represents a lower alkyl group which comprises protecting the amino group of the phenol corresponding to the compound of formula I, submitting the compound thus obtained to an alkylation (with a compound of formula Hal—CH$_2$—COOR', wherein R' is as defined hereinabove for the formula I and Hal is chlorine, bromine or iodine) and then releasing the amino group of the product thus obtained.

6 Claims, No Drawings

PROCESS FOR THE O-ALKYLATION OF N-(HYDROXY)ARALKYLPHENYLETHANOLAMINES

The present invention concerns a process for the O-alkylation of N-(hydroxy)aralkyl-phenylethanolamines, more particularly for the alkylation of the phenolic hydroxyl group of said (hydroxy)aralkylated phenylethanolamines, and intermediates used in this process.

The European Patent Specification 211721 discloses phenylethanolaminotetralins of formula

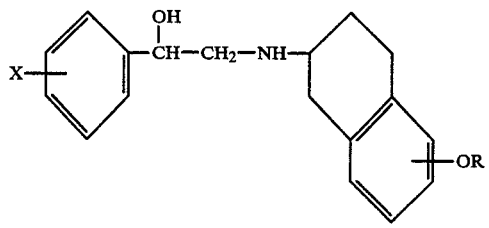

(A)

wherein X is hydrogen, halogen, a trifluoromethyl group or a lower alkyl group and R is hydrogen; a lower alkyl group unsubstituted or substituted by a cycloalkyl group of from 3 to 7 carbon atoms, a hydroxy group, a lower alkoxy, carboxy or lower carbalkoxy group; a cycloalkyl group of from 3 to 7 carbon atoms or a lower alkanoyl group and their pharmaceutically acceptable salts.

Among the methods of preparation of the products of formula (A) hereinabove there is described an O-alkylation that, starting from the 2-[(7-hydroxy-1,2,3,4-tetrahydronaphth-2-yl)amino]-1-phenylethanol or from the 2-[(7-hydroxy-1,2,3,4-tetrahydronaphth-2-yl)amino]-1-(3-chlorophenyl)ethanol, by reaction with ethyl bromoacetate gives the 2-[(7-carbethoxymethoxy-1,2,3,4-tetrahydronaphth-2-yl)amino]-1-phenylethanol or the 2-[(7-carbethoxymethoxy-1,2,3,4-tetrahydronaphth-2-yl)amino]-1-(3-chlorophenyl)ethanol. This reaction does not give yet good result because the yield of the final product is very low.

It has now been found that the above mentioned products may be obtained in higher yields by protecting the amino group of the above mentioned compound of formula A, wherein R represents hydrogen, before the alkylation and by deprotecting it then.

Thus, the present invention relates to a process for the preparation of compounds of formula

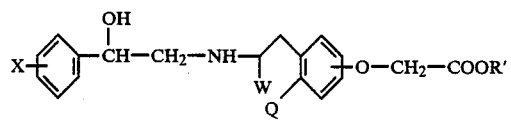

I wherein X represents hydrogen, halogen, a trifluoromethyl group or a lower alkyl group; W represents methyl, Q represents hydrogen, or W and Q, together, form an ethylene group and R' represents a lower alkyl group; and to their pharmaceutically acceptable salts, which comprises (a) protecting the amino group of a compound of the formula

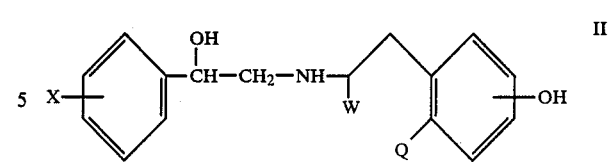

II wherein X, W and Q are as defined hereinabove, (b) submitting the compound thus obtained of formula

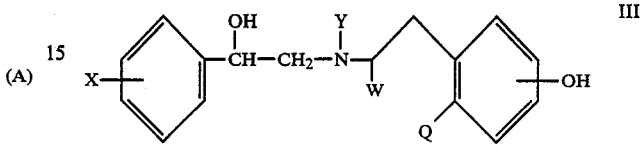

III wherein X, W and Q are as defined hereinabove and Y represents a N-protecting group, to an alkylation with a compound of formula Hal—CH$_2$—COOR', wherein R' is as defined hereinabove and Hal represents chlorine, bromine or iodine;

(c) deprotecting the amino group of the compound thus obtained of formula

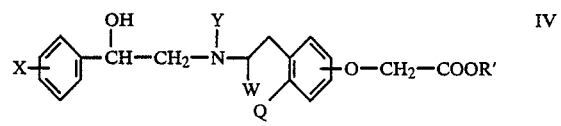

IV wherein X, Y, W, Q and R' are as defined hereinabove, and optionally transforming the product thus obtained into one of its pharmaceutically acceptable salts.

The lower alkyl group contains from 1 to 4 carbon atoms.

Among the halogens, fluorine, bromine and expecially chlorine are particularly preferred.

Among the protecting groups designated by Y, the Boc group (t.butyloxycarbonyl) and the Z group (benzyloxycarbonyl) are advantageous.

In this specification the "tetralin" and "tetralone" terms refer to the 1,2,3,4-tetrahydronaphtalene.

The preferred compounds that may be obtained by the process of the present invention of those of formula I wherein X is as defined hereinabove, more particularly 3-chloro, R' represents a methyl or ethyl group and the O—CH$_2$—COOR' group is, with respect to the Q substituent, in meta position when Q is hydrogen and in para position when W and Q, together, form an ethylene group.

Particularly prefered are the following compounds:

N-[(2R)-7-ethoxycarbonylmethoxy-1,2,3,4-tetrahydronapht-2-yl]-(2R)-2-(3-chlorophenyl)-2-hydroxyethanamine, N-[(2S)-7-ethoxycarbonylmethoxy-1,2,3,4-tetrahydronapht-2-yl]-(2R)-2-(3-chlorophenyl)-2-hydroxyethanamine, N-[(2R)-7-methoxycarbonylmethoxy-1,2,3,4-tetrahydronapht-2-yl]-(2R)-2-(3-chlorophenyl)-2-hydroxyethanamine, and their pharmaceutically acceptable salts.

Said compounds are new and show very interesting pharmacological properties.

The starting compounds of formula II are described in the literature, more particularly in the Patents EP No. 211721 (W+Q=ethylene), EP No. 66351 (W=methyl, Q=hydrogen, X=trifluoromethyl), EP No. 70134 (W=methyl, Q=hydrogen, X=halogen) or they may be easily prepared by known methods, more particularly by those of the three above mentioned patents.

The process of the present invention is carried out be reacting a compound of formula II with a suitable reagent for the protection of the amino groups as described, for example, by M. Bodanszky and al., Peptide Synthesis, 2nd Edition, John Wiley & Sons 1976, pages 18–49.

The Boc group, for example, may be introduced by reaction with di-t.butyldicarbonate in a basic medium. The Z group may be introduced according to the general procedure described by E. C. Horning, Organic Synthesis, vol. III, Wiley, New York 1955, page 167.

The compound of formula III thus obtained is then alkylated by reaction with an halide of formula Hal—CH$_2$—COOR' wherein R' and Hal are as defined hereinabove, in the presence of a basic condensing agent as a hydroxide or a carbonate of an alkali metal, for example potassium carbonate.

The removal of the protecting group Y in the compound of formula IV thus obtained is carried out according to methods described in the literature.

For example, the Boc group may be removed by treatment with trifluoroacetic acid, alone or in solution in methylene chloride or chloroform, with hydrogen chloride in ethyl acetate, with hydrogen chloride in acetic acid or with formic acid. When the removal is carried out with trifluoroacetic acid, the product of formula I is isolated as trifluoroacetate. The salt thus obtained may be neutralized with a base, for example with ammonium hydroxide, and the free base may be isolated or directly transformed into another salt, for example the hydrochloride or the hydrobromide.

The Z group may be removed, for example, by hydrogenolysis.

The compounds having the formulas III and IV hereinabove are new and represent the key intermediates of the process of the present invention.

Thus, it is another object of the present invention to provide compounds of formula

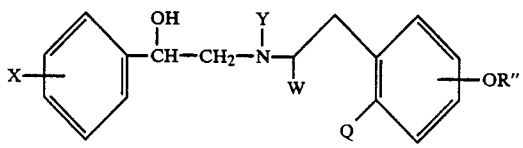

V wherein X, Y, W and Q are as defined hereinabove and R" represents hydrogen or a CH$_2$—COOR' group, wherein R' is as defined hereinabove.

The sequence of the reactions of this process does not modify the stereochemistry of the compounds involved. Thus, the process of the present invention allows to work with the racemic mixtures or with the pure optical isomers.

The following examples illustrate the invention without however limiting it. The specific optical rotation symbol is indicated as |alpha|, but it must be read [alpha]$_D^{20}$.

PREPARATION I

N-(7-hydroxy-1,2,3,4-tetrahydronaphth-2-yl)-2-(3-chlorophenyl)-2-hydroxyethanamine; SR 58523, disastereoisomer A.

An amount of 3.9 g of N-(7-hydroxy-1,2,3,4-tetrahydronaphth-2-yl)-2-(3-chlorophenyl)-2-hydroxyethanamine base, obtained in diastereoisomeric mixture 50/50 as described in Example 8 of the European Pat. No. 211721, is dissolved in 150 ml of acetone and left to crystallize overnight after the addition of some seeds. The product which precipitates is filtered, the filtrate is evaporated to one half of its volume and it is left in the refrigerator overnight; another small amount of product for a total weight of 1.8 g is obtained; m.p. 175° C. This product is recrystallized from 120 ml of acetone, then it is left to crystallize overnight in the refrigerator to obtain 1.2 g of SR 58523; m.p. 182°–184° C., as pure diastereoisomer, according to the $^{13}$C NMR (50 MHz). Its configuration is (RS,SR).

PREPARATION II

N-(7-hydroxy-1,2,3,4-tetrahydronaphth-2-yl)-2-(3-chlorophenyl)-2)hydroxyethanamine; SR 58524, diastereoisomer B.

The mother liquors of the crystallization of SR 58523, obtained in PREPARATION I, are evaporated to dryness and the residue is dissolved, with a slight warming, in 25 ml of ethyl acetate, filtered through paper, left to crystallize in the refrigerator overnight, and filtered to give 1.2 g de SR 58524; m.p. 136°–138° C., as a mixture of diastereoisomers (RR,SS)/(RS,SR) 75/25, as determined by the $^{13}$C NMR (50 MHz).

PREPARATION III

R(+)-2-amino-7-hydroxytetralin monohydrate; SR 58554.

To a solution in 550 ml of absolute ethanol of 50 g of 2-amino-7-methoxytetralin crude base, obtained from the corresponding hydrochloride (J. Chem. Soc., 1965 (April), 2636–41) by neutralisation with 10% sodium hydroxide, extraction with ethyl acetate and evaporation of the solvent, there is added a solution of 43 g of (+) mandelic acid in 550 ml of absolute ethanol. After a night at room temperature, the precipitate thus obtained is filtered and crystallized twice in absolute ethanol recovering each time the crystallized product after a night at rest at room temperature. Thus, there is obtained 34.2 g (74%) of the pure salt of (+) mandelic acid with (+)-2-amino-7-methoxytetralin; m.p. 190°–192° C. The mother-liquors of the first crystallization are separated and used for the PREPARATION IV hereinbelow. An amount of 34 g of the salt thus obtained is suspended in 300 ml of water and the reaction mixture is made alkaline with N sodium hydroxide. The base is extracted from ethyl acetate, evaporated to dryness and the residue is taken up with 260 ml of 48% hydrobromic acid. The reaction mixture is heated with reflux for three hours, evaporated to dryness under reduced pressure and the residue thus obtained is taken up with 70 ml of water. The aqueous solution is made alkaline with concentrated ammonium hydroxide, then it is cooled overnight and filtered. The R(+)-2-amino-7-hydroxytetralin (SR 58554), as a monohydrate is obtained; m.p. 143°–144° C., |alpha| = +85.1° (methanol, c=0.5%). The hydrochloride of this product has a rotatory power corresponding to that of literature (Molecular Pharmacology, 1982, 22, 281-289).

PREPARATION IV

S(−)-2-amino-7-hydroxytetralin monohydrate, SR 58555

The mother-liquors of the first crystallization of SR 58554 (PREPARATION III), are evaporated to dryness, the residue thus obtained is suspended in 300 ml of water and the suspension is made alkaline with N sodium hydroxide. The base is extracted with ethyl acetate. By following the procedure described in PREPARATION III and using the base above and the (−) mandelic acid as starting products, there is obtained the salt of (−) mandelic acid with (−)-2-amino-7-methoxytetralin (m.p. 189°–191° C.) that, by treatment with N sodium hydroxide, gives the S(−)-2-amino-7-hydroxytetralin, SR 58555, as a monohydrate; m.p. 143°–144° C., |alpha| = −86.9° (methanol, c=0.5%). The hydrochloride of this product has a rotatory power corresponding to that of the literature (Molecular Pharmacology 1982, 22, 281–289).

PREPARATION V

N-[92S)-7-hydroxy-1,2,3,4-tetrahydronaphth-2-yl]-(R)-3-chloromandelamide, SR 58587

An amount of 3.6 g of (R)-3-chloromandelic acid (Bull. Soc. Chim. Fr., 1973, 12, 3330) is reacted with 3.5 g of S(−)-2-amino-7-hydroxytetralin monohydrate (PREPARATION IV) and 7.7 g of BOP in 60 ml of anhydrous methylene chloride under nitrogen stream. An amount of 2.7 ml of triethylamine is added, the solution thus obtained is left under stirring for 5 hours at room temperature, then 400 ml of ethyl acetate are added thereto. After washing with a sodium bicarbonate solution, then with water, then with hydrochloric acid and finally with water, the organic phase is separated and evaporated to dryness. The residue thus obtained is treated with 150 ml of N sodium hydroxide and extracted with ethyl ether that is then eliminated. The aqueous phase is made acid with concentrated hydrochloric acid and extracted with ethyl acetate. The organic phase is washed with water, dried over sodium sulfate, filtered and evaporated to dryness. The oil thus obtained is purified by flash chromatography by eluting with a 70/30 mixture of ethyl acetate/cyclohexane. The N-[(2S)-7-hydroxy-1,2,3,4-tetrahydronaphth-2-yl]-(R)-3-chloromandelamide, is obtained as a very thick whitish oil that is treated with petroleum ether to give a solid having an indefinite melting point, SR 58587, |alpha| −95° (methanol, c=1%).

PREPARATION VI

N-[(2R)-7-hydroxy-1,2,3,4-tetrahydronaphth-2-yl]-(S)-3-chloromandelamide, SR 58588

By following the procedure described in PREPARATION V, by substituting the (S)-3-chloromandelic acid (Bull. Soc. Chim. Fr., 1973, 12, 3330) for the (R)-3-chloromandelic acid and the monohydrate of R(+)-2-amino-7-hydroxy-1,2,3,4-tetrahydronaphthalene (PREPARATION III) for the monohydrate of S(−)-2-amino-7-hydroxy-1,2,3,4-tetrahydronaphthalene, there is obtained the N-[(2R)-7-hydroxy-1,2,3,4-tetrahydronaphth-2-yl]-(S)-3-chloromandelamide, as a solid having an indefinite melting point; SR 58588, |alpha| = +92,5° (methanol, c=1%).

PREPARATION VII

N-[(2R)-7-hydroxy-1,2,3,4-tetrahydronaphth-2-yl]-(2S)-2-(3-chlorophenyl)-2-hydroxyethanamine, SR 58590

To a solution of 3 g of N-[(2R)-7-hydroxy-1,2,3,4-tetrahydronaphth-2-yl]-(S)-3-chloromandelamide, SR 58588, PREPARATION VI, in 40 ml of anhydrous tetrahydrofuran, heated with reflux under nitrogen stream, there is added 2.7 ml of a 10M solution of borane-methylsulfide (reagent which generates diborane consisting of a complex of borane and dimethylsulfide) in 20 ml of tetrahydrofuran, and heated for 4 hours with reflux. To the solution cooled at room temperature, there is added 25 ml of methanol and the reaction mixture is left under stirring at first 30 minutes at room temperature, then, 30 minutes with reflux. After concentration under reduced pressure and filtration, the residue is crystallized twice from isopropanol to give the N-[(2R)-7-hydroxy-1,2,3,4-tetrahydronaphth-2-yl]-(2S)-2-(3-chlorophenyl)-2-hydroxyethanamine, SR 58590; m.p. 186°–188° C.; |alpha| = +76° (methanol, c=0.5%).

PREPARATION VIII

N-[(2S)-7-hydroxyl-1,2,3,4-tetrahydronaphth-2-yl]-(2R)-2-(3-chlorophenyl)-2-hydroxyethanamine, SR 58589

By following the procedure described in PREPARATION VII, and utilizing as starting product 2.5 g of SR 58587, PREPARATION V, the N-[(2S)-7-hydroxy-1,2,3,4-tetrahydronaphth-2-yl]-(2R)-2-(3-chlorophenyl)-2-hydroxyethanamine, SR 58589, is obtained; m.p. 185°–187° C.; |alpha| = −78.5° (methanol, c=0.5%).

PREPARATION IX

N-[N-[(2R)-7-hydroxy-1,2,3,4-tetrahydronaphth-2-yl]-(R)-3-chloromandelamide, SR 58533

To a suspension of 2.6 g of (R)-2-amino-7-hydroxytetralin hydrochloride, PREPARATION III, 2.4 g of (R)-3-chloromandelic acid and 5.2 g of BOP in 60 ml of anhydrous methylene chloride, there is added slowly 3.6 ml of triethylamine, then the solution thus obtained is left under stirring at room temperature for 3 hours. A volume of 50 ml of a saturated sodium chloride solution is added thereto, and the reaction mixture is left under stirring for 30 minutes at room temperature. After addition of 200 ml of ethyl acetate the phases are separated. The organic phase is washed twice with 30 ml of 2N hydrochloric acid and then twice with 30 ml of a saturated sodium chloride solution. The organic solution is dried over sodium sulfate, then filtered and evaporated to dryness. The oil thus obtained is purified by flash chromatography by eluting with 55/45 mixture of ethyl acetate/cyclohexane. A doughy solid is obtained that is taken up with 20 ml of ethyl ether from which the product crystallizes. After addition of 10 ml of cyclohexane, the product is filtered, washed with a 2/1 mixture of cyclohexan/ethyl ether and dried under reduced pressure at 50° C. A pure stereoisomer according to $^{13}$C NMR at 60 MHz is obtained; m.p. 132°–134° C., |alpha| = +24.9° (methanol, c=1%. After a further purification by chromatography, the enantiomerically and chemically pure N-[(2R)-7-hydroxy-1,2,3,4-tetrahydronaphth-2-yl]-(R)-3-chloromandelamide, SR 58533, is obtained; m.p. 143°–147° C.; |alpha| = +35,1° (methanol, c=1%).

PREPARATION X

N-[(2S)-7-hydroxy-1,2,3,4-tetrahydronaphth-2-yl]-(S)-3-chloromandelamide, SR 58574

By following the procedure described in PREPARATION IX and substituting the (S)-3-chloromandelic acid for the (R)-3-chloromandelic acid and the (S)-2-amino-7-hydroxytetralin hydrochloride, PREPARATION IV, for the (R)-2-amino-7-hydroxytetralin hydrochloride, the N-[(2S)-7-hydroxy-1,2,3,4-tetrahydronaphth-2-yl]-(S)-3-chloromandelamide, SR 58574, is obtained; m.p. 145°–146° C.; |alpha| = −34.2° (methanol, c=1%).

PREPARATION XI

N-[(2R)-7-hydroxy-1,2,3,4-tetrahydronaphth-2-yl]-(2R)-2-(3-chlorophenyl)-2-hydroxyethanamine hydrochloride, SR 58572 A By submitting the product obtained in PREPARATION IX to a reduction with borane-methylsulfide as described in PREPARATION VII, there is obtained the N-[(2R)-7-hydroxy-1,2,3,4-tetrahydronaphth-2-yl]-(2R)-2-(3-chlorophenyl)-2-hydroxyethanamine base. This product is dissolved in acetone, treated with a saturated solution of hydrogen chloride in isopropanol, to give after filtration, a residue which is crystallized twice from isopropanol. The product so obtained, cooled, filtered and washed at first with isopropanol then with acetone gives the N-[(2R)-7-hydroxy-1,2,3,4-tetrahydronaphth-2-yl]-(2R)-2-(3-chlorophenyl)-2-hydroxyethanamine hydrochloride, SR 58572 A; m.p. 203°–205° C.; |alpha| = +36.4° (methanol, c=1%).

PREPARATION XII

N-[(2S)-7-hydroxy-1,2,3,4-tetrahydronaphth-2-yl]-(2S)-2-(3-chlorophenyl)-2)-hydroxyethanamine hydrochloride, SR 58575 A By submitting the product obtained in PREPARATION X to a reduction with borane-methylsulfide as described in PREPARATION VII, there is obtained the N-[(2S)-7-hydroxy-1,2,3,4-tetrahydronaphth-2-yl]-(2S)-2-(3-chlorophenyl)-2)-hydroxyethanamine base which, according to the procedures described in PREPARATION XI, gives the corresponding hydrochloride, SR 58575 A; m.p. 203°–205° C.; |alpha| = −35.8° (methanol, c=1%).

EXAMPLE 1

N-t.butyloxycarbonyl-N-(7-hydroxy-1,2,3,4-tetrahydronaphth-2-yl)-2-(3-chlorophenyl)-2-hydroxyethanamine; diastereoisomer A An amount of 1.5 g of SR 58523, obtained as described in PREPARATION I, is dissolved in 100 ml of dioxane. To the solution thus obtained there are added 5.1 ml of N sodium hydroxide and 5.1 mM of di-t.butyldicarbonate, at room temperature. The mixture is stirred for 1 hour at room temperature, for 2 hours at 40° C. and then overnight at room temperature. After evaporation under reduced pressure the residue is taken up with 150 ml of ethyl ether, the ethereal solution is washed with water, dried and the ether is removed to dryness. The residue has an ¹NMR which confirms the obtention of the above mentioned product.

¹NMR: ppm (DMSO D6) 1.32 (9H,s) 1.55–2.12 (2H,m) 2.25–2.82 (4H,m) 3.17 (2H,m) 3.45–3.90 (1H,m) 4.50–4.87 (1H,s, J=5 Hz) 5.37 (1H,d,J=5 Hz) 6.17–6.48 (2H,m) 6.57–6.82 (1H,m) 7.05–7.30 (4H,m) 8.80 (1H,s).

EXAMPLE 2

N-t.butyloxycarbonyl-N-(7-hydroxy-1,2,3,4-tetrahydronapht-2-yl)-2-(3-chlorophenyl)-2-hydroxyethanamine; diastereoisomer B An amount of 1.5 g of SR 58524, obtained as described in PREPARATION II, is dissolved in 100 ml of dioxane. To the solution thus obtained there are added 5.1 ml of N sodium hydroxide and 5.1 mM of di-t.butyldicarbonate at room temperature. The mixture is stirred for 1 hour at room temperature, for 2 hours at 40° C. and then overnight at room temperature. The mixture is evaporated under reduced pressure, then the residue is taken up with 150 ml of ethyl ether, the ethereal solution is washed with water, dried and evaporated to dryness. The residue is analyzed by ¹H NMR and the obtention of the above mentioned product is confirmed.

¹H NMR: ppm (DMSO D6) 1.32 (9H,s) 1.55–2.12 (2H,m) 2.25–2.82 (4H,m) 3.17 (2H,m) 3.45–3.90 (1H,m) 4.50–4.87 (1H,s, J=5 Hz) 5.37 (1H,d, J=5 Hz) 6.17–6.48 (2H,m) 6.57–6.82 (1H,m) 7.05–7.30 (4H,m) 8.80 (1H,s).

EXAMPLE 3

N-(7-ethoxycarbonylmethoxy-1,2,3,4-tetrahydronaphth-2-yl)-2-(3-chlorophenyl)-2-hydroxyethanamine trifluoroacetate; SR 58538 A, diastereoisomer A (a) The product obtained in Example 1 is dissolved in 190 ml of acetone and to the solution thus obtained there is added 5.4 ml of ethyl bromoacetate and 6.36 g of potassium carbonate. The mixture is stirred with reflux for 6 hours, filtered and evaporated to dryness. The resulting residue is taken up with ethyl ether and the solution is filtered. By evaporation of the solvent, the N-t.butyloxycarbonyl-N-(7-ethoxycarbonylmethoxy-1,2,3,4-tetrahydronaphth-2-yl)-2-(3-chlorophenyl)-2-hydroxyethanamine; diastereoisomer A, is obtained.

¹H NMR: ppm (DMSO D6) 1.22 (3H,t,J=7 Hz) 1.35 (9H,s) 1.67–2.11 (2H,m) 2.52–2.98 (4H,m) 3.07–3.32 (2H,m) 3.55–3.87 (1H,m) 4.10 (2H,q,J=7 Hz) 4.51–4.87 (1H,m) 4.61 (2H,s) 5.25–5.62 (1H,m) 6.40–6.67 (2H,m) 6.77–7.02 (1H,m) 7.15–7.40 (4H,m).

(b) A solution of the product of step (a) in 125 ml of methylene chloride, is cooled at 0°–5° C. and then 8 ml of trifluoroacetic acid dissolved in 40 ml of methylene chloride are added thereto. The mixture is stirred for 15 minutes in the cold and for 2 hours at room temperature. Then it is evaporated to dryness under reduced pressure at 40° C. The residue is crystallized from ethyl ether to obtain 3.9 g of a product melting at 157°–159° C. This product crystallized from a mixture of 7.5 ml of ethyl acetate and 15 ml of ethyl ether gives 3.3 g of SR 58538 A, diastereoisomer A; m.p. 156°–158° C. (total yield starting from SR 58523: 42%).

EXAMPLE 4

N-(7-ethoxycarbonylmethoxy-1,2,3,4-tetrahydronaphth-2-yl)-2-(3-chlorophenyl)-2-hydroxyethanamine trifluoroacetate; SR 58539 A, diastereoisomer B (a) The product obtained in Example 2 is dissolved in 200 ml of acetone and to the solution there is added 5.6 ml of ethyl bromoacetate and 6.63 g of potassium carbonate. The mixture is stirred with reflux for 6 hours, filtered and evaporated to dryness. The residue is taken up with ethyl ether, the ethereal solution is filtered and the solvent is evaporated. Thus, there is obtained the N-t.butyloxycarbonyl-N-(7-ethoxycarbonylmethoxy-1,2,3,4-tetrahydronaphth-2-yl)-2-(3-chlorophenyl)-2-hydroxyethanamine; diastereoisomer B.

$^1$H NMR: ppm (DMSO D6) 1.22 (3H,t,J=7 Hz) 1.35 (9H,s) 1.67–2.11 (2H,m) 2.52–2.98 (4H,m) 3.07–3.32 (2H,m) 3.55–3.87 (1H,m) 4.10 (2H,q,J=7 Hz) 4.51–4.87 (1H,m) 4.61 (2H,s) 5.25–5.62 (1H,m) 6.40–6.67 (2H,m) 6.77–7.02 (1H,m) 7.15–7.40 (4H,m).

(b) A solution of the product of step (a) in 130 ml of methylene chloride is cooled at 0°–5° C. and then 12.7 ml of trifluoroacetic acid dissolved in 40 ml of methylene chloride, is added thereto. The mixture is stirred for 15 minutes in the cold and for 2 hours at room temperature. Then it is evaporated to dryness under reduced pressure at 40° C. The residue is crystallized from ethyl ether to give 5 g of a product melting at 132°–134° C. which is dissolved in the warm in 9 ml of ethyl acetate. To this solution there is added 35 ml of ethyl ether and, after cooling, the precipitate is filtered. Thus an amount of 4.1 g of SR 58539 A is obtained; m.p. 134°–136° C., (total yield starting from SR 58524: 49%).

EXAMPLE 15

N-(7-ethoxycarbonylmethoxy-1,2,3,4-tetrahydronapht-2-yl)-2-(3-chlorophenyl)-2-hydroxyethanamine hydrochloride; SR 58539 B, diastereoisomer B An amount of 7.5 g of SR 58539 A, prepared as described in Example 4, is suspended in water with 10 of 15% ammonium hydroxide. The suspension is extracted with ethyl ether, and the ether phase is washed with water. After evaporation of the ether, the residue is dissolved in ethanol and the solution is treated with a solution of hydrogen chloride in ethanol. After evaporation of the ethanol, the residue is taken up with ethyl ether and a solid product is obtained that is crystallized from ethyl acetate. Thus, there is obtained 3.1 g (50%) of the above mentioned product; m.p. 137°–139° C.; pure diastereoisomer according to $^{13}$C NMR (50 MHz). Its configuration is (RR,SS).

EXAMPLE 6

N-(7-ethoxycarbonylmethoxy-1,2,3,4-tetrahydronapht-2-yl)-2-(3-chlorophenyl)-2-hydroxyethanamine hydrochloride; SR 58538 B, diastereoisomer A An amount of 5.1 g of SR 58538 A, prepared as described in Example 3, is suspended in water with 7 ml of 15% ammonium hydroxide. The suspension is extracted with ether, the ether phase is washed with water and, after evaporation of the ether, the residue is dissolved in ethanol and the solution is treated with a solution of hydrogen chloride in ethanol. After evaporation of the ethanol, the residue is taken up with ethyl ether and the product so obtained is crystallized from a mixture of ethanol/ethyl ether. Thus, there is obtained 3.4 g (79%) of the above mentioned product; m.p. 124°–126° C.; pure diastereoisomer according to $^{13}$C NMR (50 MHz). Its configuration is (RS,SR).

EXAMPLE 7

N-t.butyloxycarbonyl-N-(7-hydroxy-1,2,3,4-tetrahydronaphth-2-yl)-2-(3-chlorophenyl)-2-hydroxyethanamine; diastereoisomer A To a solution of 4.9 g of SR 58523, obtained as described in PREPARATION I, in 200 ml of t.butanol there are added 16.9 ml of N sodium hydroxide and 16.9 mM of di-t.butyldicarbonate, at room temperature. The mixture is stirred for 1 hour at room temperature, for 2 hours at 40° C. and then overnight at room temperature. The mixture is taken up with 350 ml of ethyl ether, the ether solution is washed with water, dried and evaporated to dryness. The residue is analysed by $^1$H NMR and the obtention of the above mentioned product, identical with the product of Example 1, is confirmed.

EXAMPLE 8

N-t.butyloxycarbonyl-N-(7-hydroxy-1,2,3,4-tetrahydronaphth-2-yl)-2-(3-chlorophenyl)b 2-hydroxyethanamine; diadstereoisomer B To a solution of 5.1 g of SR 58524, obtained as described in PREPARATION II, in 200 ml of t.butanol there are added 17.6 ml of N sodium hydroxide and 17,6 mM of di-t.butyldicarbonate, at room temperature. The mixture is stirred for 1 hour at room temperature, for 2 hours at 40° C. and then overnight at room temperature. The mixture is taken up with 350 ml of ethyl ether, the ether phase is washed with water and dried and evaporated to dryness. The residue is analysed by $^1$H NMR and the obtention of the above mentioned product, identical with the product of Example 2, is confirmed.

EXAMPLE 9

N-[2-(4-ethoxycarbonylmethoxyphenyl)-1-methylethyl]-2-(3-chlorophenyl)-2-hydroxyethanamine trifluoroacetate (a) To a mixture of 1.6 g of N-[2-(4-hydroxyphenyl)-1-methylethyl]-2-(3-chlorophenyl)-2-hydroxyethanamine (prepared as described in Example 2 of EP 70134 but using, a reducing agent, sodium cyanoborohydride instead of sodium borohydride) and 5.5 ml of N sodium hydroxide in 50 ml of dioxane, there is added, dropwise and at room temperature, 1.2 g of di-t.butyldicarbonate dissolved in 10 ml of dioxane. The mixture is stirred for 2 hours at 40° C., then overnight at room temperature. After dilution with ethyl ether, the organic solution is washed three times with 20 ml of water and dried over sodium sulfate. The organic phase is concentrated under reduced pressure to obtain 2.5 g of N-t.butyloxycarbonyl-N-[2-(4-hydroxyphenyl)-1-methylethyl]-2-(3-chlorophenyl)-2-hydroxyethanamine, in form of an oily product that is used as such.

(b) A mixture of 2.5 g of the product of step (a), 3.1 g of ethyl bromoacetate and 2.5 mg of potassium carbonate in 80 ml of acetone is heated with reflux for 6 hours. After cooling, the inorganic salts which precipitate are filtered off and the solution is evaporated under reduced pressure. The residue is purified by chromatography on a silica gel column (eluent a 7/3 mixture of cyclohexane/ethyl acetate). Thus there is obtained 2 g of N-t.butyloxycarbonyl-N-[2-(4-ethoxycarbonylmethoxyphenyl)-1-methylethyl]-2-(3-chlorophenyl)-2-hydroxyethanamine, as a pure product. Yellow oil. Yield 70%.

NMR (CDCl$_3$) 0.87–1.52 (15H,m) 2.32–2.82 (2H,m) 3.00–3.38 (2H,m) 3.70–4.25 (2H,m) 4.10 (2H,q, J=7 Hz) 4.42 (2H,s) 4.35–4.87 (2H,m) 6.52–7.00 (4H,m) 7.05 (3H,s) 7.22 (1H,s).

IR 1650–1690 cm$^{-1}$ and 1735–1760 cm$^{-1}$ (c) To a solution of 1.5 g of the product of step (b) in 10 ml of methylene chloride, there is added 10 ml of trifluoroacetic acid at 0° C. The mixture is stirred for 3 hours at room temperature then it is concentrated under reduced pressure. After washing the residual oil with ethyl ether, 1.4 g of N-[2-(4-ethoxycarbonylmethoxyphenyl)-1-methylethyl]-2-(3-chlorophenyl)-2-hydroxyethanamine trifluoroacetate, is obtained, as a yellow oil. Yield 90%.

$^1$H NMR: ppm (DMSO D6) 1.17 (3H,t, J=7 Hz) 1.07 (3H,d, J=6 Hz) 2.50–2.80 (1H,m) 2.82–3.60 (4H,m) 4.1 (2H, q, J=7 Hz) 4.65 (2H,s) 4.77–5.07 (1H,m) 5.12–5.92 (3H,m) 6.95 (4H,q, J=8 Hz) 7.3 (3H,s) 7.4 (1H,s).

IR 1670 cm$^{-1}$, 1750 cm$^{-1}$.

The product thus obtained may be easily saponified with the calculated amount of an alkaline agent and transformed into the corresponding free acid.

EXAMPLE 10

The procedure described in Example 9, step (a), is exactly followed, then (b) the product thus obtained is reacted with methyl bromoacetate under the conditions described in Example 9, step (b), to obtain the N-t.butyloxycarbonyl-N-[2-(4-methoxycarbonylmethoxyphenyl)-1-methylethyl]-2-(3-chlorophenyl)-2-hydroxyethanamine; and (c) the product thus obtained is treated with the trifluoroacetic acid under the conditions described in Example 9, step (c), to obtain the N-[2-(4-methoxycarbonylmethoxyphenyl)-1-methylethyl]-2-(3-chlorophenyl)-2-hydroxyethanamine trifluoroacetate.

EXAMPLE 11

By neutralization of the product obtained in Example 10 with ammonium hydroxide, as described in Example 6, and salification with a solution of hydrogen bromide (instead of hydrogen chloride) in ethanol, the N-[2-(4-methoxycarbonylmethoxyphenyl)-1-methylethyl]-2-(3-chlorophenyl)-2-hydroxyethanamine hydrobromide is obtained.

EXAMPLE 12

N-[(2S)-7-ethoxycarbonylmethoxy-1,2,3,4-tetrahydronapht-2-yl]-(2R)-2-(3-chlorophenyl)-2-hydroxyethanamine hydrochloride; SR 58611 A (a) An amount of 1.8 g of SR 58589, obtained as described in PREPARATION VIII, is dissolved in 12 ml of dimethylformamide and after addition of 4 ml of triethylamine, the solution thus obtained is stirred for 10 minutes at room temperature. An amount of 1.36 g of di-t-butyldicarbonate is added thereto and the reaction mixture is left under stirring for 3 hours at room temperature. After addition of 50 ml of water, the mixture is extracted three times with 70 ml of ethyl ether. The organic phase is washed with water, dried and evaporated to dryness to give 2.4 g (100%) of N-t.butyloxycarbonyl-N-[(2S)-7-hydroxy-1,2,3,4-tetrahydronaphth-2-yl]-(2R)-2-(3-chlorophenyl)-2-hydroxyethanamine, as an oily product.

(b) The product thus obtained is dissolved in 90 ml of acetone and 1.9 ml of ethyl bromoacetate, then 2.34 g of anhydrous potassium carbonate are added thereto. The reaction mixture is heated with reflux for 6 hours and, after filtration, the acetone is evaporated under reduced pressure. The residue is dissolved in 20 ml of methylene chloride and to the solution thus obtained, cooled at 0°–5° C., there is added 4.97 g of trifluoroacetic acid dissolved in 10 ml of methylene chloride. The reaction mixture is stirred for 4 hours at room temperature then neutralized with a sodium bicarbonate solution. After separation of the organic phase, the mixture is washed with water and evaporated to dryness. The product thus obtained is purified by chromatography on a silica gel column (elution with ethyl acetate). The solution of the product thus obtained in ethanol is treated with a solution of hydrochloric acid in ethanol. After evaporation of the solvent, 0.55 g (22%) of N-[(2S)-7-ethoxycarbonylmethoxy-1,2,3,4-tetrahydronaphth-2-yl]-(2R)-2-(3-chlorophenyl-2-hydroxyethanamine hydrochloride is obtained as a vitreous solid; SR 58611 A, |alpha| = −72.9° (c=0,5%, methanol).

$^1$H NMR: ppm (DMSO D6) 1.2 (3H,t, J=7 Hz) 4.1 (3H,q, J=7 Hz) 4.62 (2H,s) 5.0 (1H,m)

IR (Kbr): 1755 cm$^{-1}$, 1612 cm$^{-1}$, 1203 cm$^{-1}$.

In vitro, this product inhibits the spontaneous motility of the rat colon (EP 255 415), with a IC$_{50}$ of 3.5 (confidence limits: 2.6–4.7) 0.10$^{-9}$M.

In vivo, in the intestinal motility test in the anesthetised rat (EP 255 415), SR 58611 A is active with a ID$_{50}$ of 13.0 (10.0–19.0) mcg/kg i.v.

Moreover, this product is totally inactive on the isolated guinea-pig atrium and very poorly active on the isolated rat uterus.

EXAMPLE 13

N-[(2R)-7-ethoxycarbonylmethoxy-1,2,3,4-tetrahydronapht-2-yl]-(2R)-2-(3-chlorophenyl)-2-hydroxyethanamine hydrochloride; SR 58612 A (a) An amount of 2 g of SR 58572 A, PREPARATION XI, is suspended in water and concentrated ammonium hydroxide is added thereto. The mixture is extracted with a 10% V/V solution of ethanol in ethyl acetate, the dried organic phase is evaporated to give 1.6 g of N-[(2R)-7-hydroxy-1,2,3,4-tetrahydronaphth-2-yl]-(2R)-2-(3-chlorophenyl)-2-hydroxyethanamine base. By operating as described in Example 12(a), 2.1 g (100%) of N-t.butyloxycarbonyl-N-([(2R)-7-hydroxy-1,2,3,4-tetrahydronaphth-2-yl]-(2R)-2-( 3-chlorophenyl)-2-hydroxyethanamine is obtained as an oily residue.

(b) By operating as described in Example 12 (b), and starting from the above product, there is obtained 0.6 g (27%) of the N-[(2R)-7-ethoxycarbonylmethoxy-1,2,3,4-tetrahydronaphth-2-yl]-(2R)-2-(3-chlorophenyl)-2-hydroxyethanamine hydrochloride; SR 58612 A; m.p. 164°–166° C.; |alpha| = +32.58° (c=1%, methanol).

In vitro, this product inhibits the spontaneous motility of the rat colon (EP 255 415), with a IC$_{50}$ of 2.7 (confidence limits: 2.0–3.5).10$^{-9}$M.

In vivo, in the intestinal motility test in the anesthetised rat (EP 255 415), SR 58612 A is active with a ID$_{50}$ of 7.7 (5.7–10.0) mcg/kg i.v.

Moreover, this product is totally inactive on the isolated guinea-pig atrium and poorly active on the isolated rat uterus.

EXAMPLE 14

N-[(2S)-7-ethoxycarbonylmethoxy-1,2,3,4-tetrahydronapht-2-yl]-(2S)-2-(3-chlorophenyl)-2-hydroxyethanamine hydrochloride; SR 58613 A (a) An amount of 2 g of SR 58575 A, PREPARATION XII, is suspended in water and after addition of concentrated ammonium hydroxide, the suspension is extracted with a 10% v/v solution of ethanol in ethyl acetate and the solvent is evaporated off to give 1.6 g of N-[(2S)-7-hydroxy-1,2,3,4-tetrahydronaphth-2-yl]-(2S)-2-(3-chlorophenyl)-2-hydroxyethanamine base. By operating as described in Example 12(a), there is obtained 2.1 g (100%) of N-t.butyloxycarbonyl-N-[(2S)-7-hydroxy-1,2,3,4-tetrahydronaphth-2-yl]-(2S)-2-(3-chlorophenyl)-2-hydroxyethanamine as an oily residue.

(b) By operating as described in Example 12(b) and starting from the product above, there is obtained 0.4 g (18%) of the N-[(2S)-7-ethoxycarbonylmethoxy-1,2,3,4-tetrahydronaphth-2-yl]-(2S)-2-(3-chlorophenyl)-2-hydroxyethanamine hydrochloride; SR 58613 A; m.p. 164°–166° C.; |alpha|= −34.3° (c=1%, methanol).

EXAMPLE 15

N-[(2R)-7-methoxycarbonylmethoxy-1,2,3,4-tetrahydronaphth-2-yl]-(2R)-2-(3-chlorophenyl)-2-hydroxyethanamine hydrochloride; SR 58636 A A solution of 4.6 g of N-t.butyloxycarbonyl-N-[(2R)-7-hydroxy-1,2,3,4-tetrahydronaphth-2-yl]-(2R)-2-(3-chlorophenyl)-2-hydroxyethanamine, obtained as described in Example 13(a), in 100 ml of acetone is treated with 1.5 g of anhydrous potassium carbonate, then refluxed for 30 minutes. The mixture is cooled and 5.3 g of anhydrous potassium carbonate, 0.9 g of potassium iodide and 5.9 g of methyl bromoacetate are added thereto. The reaction mixture is refluxed for 5 hours, then it is filtered and evaporated to dryness. The residue is taken up with ethyl ether and the ethereal solution is washed with water, dried over sodium sulfate, and evaporated. The residue is dissolved in 40 ml of methylene chloride. The solution thus obtained is cooled to 0°–5° C. and a cold solution of 20.7 g of trifluoroacetic acid in 30 ml of methylene chloride is added thereto. The reaction mixture is stirred at 0° C. for half an hour then for 5 hours at room temperature. The solution is washed with a sodium bicarbonate solution and then with water. After drying over sodium sulfate, the solvent is evaporated off and the crystalline residue is filtered with ether. After crystallization from ethyl acetate, 50 ml of water and 10 ml of ammonium hydroxide are added to the solid so obtained and the mixture is extracted with ethyl acetate, dried and evaporated to dryness. The residue is taken up with 10 ml of ethyl acetate and the solution so obtained is acidified with a solution of hydrogen chloride in isopropanol. The product which precipitates is filtered and washed with a small amount of ethyl acetate and ether to give 0.7 g (15%) of N-[(2R)-7-methoxycarbonylmethoxy-1,2,3,4-tetrahydronaphth-2-yl]-(2R)-2-(3-chlorophenyl)-2-hydroxyethanamine hydrochloride; SR 58636 A; m.p. 152°–154° C.; |alpha|= +32.4° (c=1%, methanol).

We claim:

1. A process for the preparation of compounds of formula

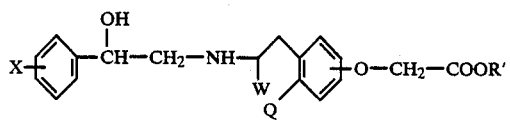

wherein X is hydrogen, halogen, a trifluoromethyl group or a lower alkyl group; W represents methyl, Q represents hydrogen or W and Q, together, form an ethylene group and R' represents a lower alkyl group and of their pharmaceutically acceptable salts, which comprises (a) protecting the amino group of a compound of formula

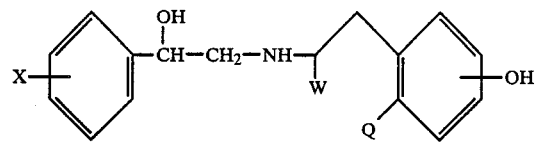

wherein X, W and Q are as defined hereinabove;

(b) submitting the compound thus obtained of formula

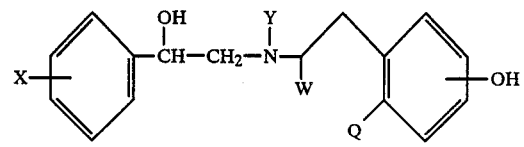

wherein X, W and Q are as defined hereinabove and Y is a N-protecting group, to an alkylation with a compound of formula Hal—CH₂COOR', wherein R' is as defined hereinabove and Hal is chlorine, bromine or iodine;

(c) deprotecting the amino group of the compound thus obtained of formula

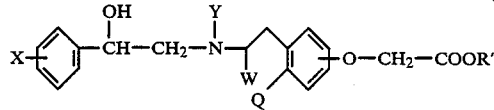

wherein X, Y, W, Q and R' are as defined hereinabove; and optionally transforming the product thus obtained into one of its pharmaceutically acceptable salts.

2. A process according to claim 1 in which the protecting group is benzyloxycarbonyl or t.butyloxycarbonyl.

3. A process according to claim 1 in which the compound of formula Hal—CH —COOR' is methyl or ethyl bromoacetate.

4. A process according to claim 1 wherein the prepared compounds are N-[(2R)-7-ethoxycarbonylmethoxy-1,2,3,4-tetrahydronaphth-2-yl]-(2R)-2-(3-chlorophenyl)-2-hydroxyethanamine or a pharmaceutically acceptable salt thereof.

5. A process according to claim 1 wherein the prepared compounds are N-[(2S)-7-ethoxycarbonylmethoxy-1,2,3,4-tetrahydronaphth-2-yl]-(2R)-2-(3-chlorophenyl)-2-hydroxyethanamine or a pharmaceutically acceptable salt thereof.

6. A process according to claim 1 wherein the prepared compounds are N-[(2R)-7-methoxycarbonylmethoxy-1,2,3,4-tetrahydronaphth-2yl]-(2R)-2-(3-chlorophenyl)-2-hydroxyethanamine or a pharmaceutically acceptable salt thereof.

* * * * *

UNITED STATES PATENT AND TRADEMARK OFFICE
CERTIFICATE OF CORRECTION

PATENT NO. : 4,927,955
DATED : May 22, 1990
INVENTOR(S) : Robert Boigegrain, Roberto Cecchi & Sergio Boveri It is certified that error appears in the above-identified patent and that said Letters Patent is hereby corrected as shown below:

Column 3, line 9, delete "be" and insert --by--;
Column 4, line 3, delete "disastereoisomer" and insert --diastereoisomer--;
Column 5, line 26, delete "92S)" and insert --(2S)--;
Column 6, line 39, delete "N-[N-" and insert --N-[--;
Column 9, line 25, delete "15" and insert --5--;
Column 12, line 14, delete "0.10$^{-9}$M" and insert --.10$^{-9}$M--;
Column 14, line 46, delete "Hal-CH-COOR'" and insert --Hal-CH$_2$-COOR'--.

Signed and Sealed this

Seventh Day of July, 1992

Attest:

DOUGLAS B. COMER

Attesting Officer     Acting Commissioner of Patents and Trademarks